United States Patent [19]

Shvartsman

[11] 4,300,101

[45] Nov. 10, 1981

[54] MULTIPLE PARALLEL INPUT NOISE REDUCTION SYSTEM

[75] Inventor: Vladimir A. Shvartsman, Louisville, Ky.

[73] Assignees: Nancy Flowers; Brian M. Kennelly, both of Louisville, Ky. ; part interest to each

[21] Appl. No.: 109,288

[22] Filed: Jan. 3, 1980

[51] Int. Cl.¹ .............................................. H03G 3/24
[52] U.S. Cl. .................................... 330/149; 330/136
[58] Field of Search .................. 330/136, 149, 124 R, 330/299; 328/165

[56] References Cited

U.S. PATENT DOCUMENTS

| 2,920,281 | 1/1960 | Appert et al. | 330/124 R |
| 3,126,449 | 3/1964 | Shirman | 179/1 |
| 4,152,659 | 5/1979 | Gordon | 330/9 |
| 4,156,202 | 5/1979 | Takahashi | 328/163 |

OTHER PUBLICATIONS

"How to Measure Noise That Is Quieter Than Your Preamp", *Application Note 127* (1974), Princeton Applied Research Corporation, Princeton, New Jersey.

*Primary Examiner*—James B. Mullins
*Attorney, Agent, or Firm*—Schuyler, Banner, Birch, McKie & Beckett

[57] ABSTRACT

A noise reduction system having a multiple number of parallel inputs amplifies a low level input signal and reduces noise. The noise reduction system includes an analog averaging circuit connected to the parallel inputs for amplifying the input signals and combining the parallel amplified input signals to generate an output signal. The parallel amplified input signals are examined for polarity by a digital logic averaging circuit. If all the parallel amplified input signals are positive or negative, respectively, the digital logic averaging circuit generates a coincidence signal. The coincidence signal then is used to adjust the gain of a variable gain amplifier connected to the output of the analog averaging circuit. The variable gain amplifier therefore amplifies those portions of the output signal of the analog averaging circuit corresponding to the true low level input signal.

6 Claims, 2 Drawing Figures

MULTIPLE PARALLEL INPUT NOISE REDUCTION SYSTEM

BACKGROUND OF THE INVENTION

The present invention is directed to a noise reduction system, more particularly, a multiple parallel input noise reduction system for eliminating noise in order to detect small input signals.

In many different fields, it is frequently necessary to detect and measure very small input signals and for preventing the transmission of noise. In fact, in many instances, the noise signals themselves may even be larger than the input signals which it is desired to detect and measure. For example, electrical signals are generated as a result of the conduction system of the heart of the human body. These electrical signals are very low level signals which are ordinarily not detectable by the usual recording means because of the magnitude of the interfering noise. Similarly, it is often desirable to detect other small biologic signals like those arising from the central nervous system as well as signals in the field of space exploration, sound engineering, electron spin resonance devices, photochemical measurements, communication systems, etc. The sensitivity of any recording system is limited by the level of input noise as well as the amplifier noise which is generated in any high fidelity recording of small input signals.

A number of different techniques are known in the art for reducing noise in low level signal measurements. For example, computer techniques have been developed to improve signal to noise ratio by applying serial signal/digital averaging techniques. Signal averaging techniques can be used to measure signals which are smaller than the noise signals generated in amplifiers. These latter techniques generally use the classical cross correlation principle which is generally known in the art. A general discussion of such a noise reduction technique can be found in the article "How To Measure Noise That Is Quieter Than Your Pre-Amp", Application Note 127 (1974), Princeton Applied Research Corporation, Princeton, New Jersey.

The signal averaging techniques implemented by computer systems have a number of major disadvantages. First of all, these systems lack the ability to detect moment-to-moment changes in the true input signal configuration, thereby introducing errors in amplitude, duration, etc. of the input signal. Also, these systems have a low efficiency rating. For example, if a signal has 100 Hz components and the period from the reference signal varies with the standard deviation of plus or minus 0.45 milliseconds, the resultant amplitude of the digitally averaged signal will be approximately half the true amplitude of the original signal with no noise contamination. Finally, signal averaging systems cannot generate on-line information because of the inevitable delay implicit in the signal sampling and averaging technique. Moreover, the necessary storage elements required in implementing the signal averaging technique complicates the design of such systems and greatly adds to the cost of their construction.

In U.S. Pat. No. 3,126,449 issued to J. Shirman on Mar. 24, 1964, a noise discriminator circuit is shown having a logic circuit for opening a gate to pass the input signal in the event that the input has certain frequency characteristics. The logic circuitry includes a plurality of parallel channels for passing signals having the selected frequency characteristics and logically combining these signals to open the gate to pass the input signal. As a result, this circuit discriminates against input signal noise.

Several other patents also show related noise reduction systems. For example, U.S. Pat. No. 2,920,281 issued to Appert et al discloses a circuit for reducing noise by connecting a pair of amplifiers in parallel. In this regard, it is well known in the art that the parallel connection of a plurality of amplifiers, transistors, etc. reduces input noise by a factor corresponding to the number of parallel amplifiers, transistors, etc. Peak level detectors for detecting the positive and/or negative peak levels of impulsive noise in the input signal are also known in the art as illustrated by U.S. Pat. No. 4,156,202 issued to Takahashi on May 22, 1979.

SUMMARY OF THE INVENTION

It is a primary object of the present invention to provide a noise reduction system for eliminating noise in low level signal systems. In this regard, it is an object of the present invention to provide a multiple parallel input noise reduction system in which the disadvantages of signal serial averaging techniques, correlation techniques, peak level detection, etc. are overcome.

It is an additional object of the present invention to provide a noise reduction system which reduces noise while at the same time detecting moment-to-moment changes in the input signal thereby eliminating errors in amplitude, duration, etc. The noise reduction system of the present invention further provides on-line information related to the input signal.

Finally, it is an object of the present invention to provide a noise reduction system which is simple in design and inexpensive to manufacture.

The noise reduction system of the present invention is a multiple parallel input analog logic averaging circuit. A number of parallel inputs are connected to the circuit to provide parallel input signals. For example, if the present invention is employed to measure electrical signals from the heart of a human body, a number of closely spaced surface electrodes could be employed which detect the electrical signals generated by the heart. Once detected, these electrical signals would be supplied to the multiple parallel inputs of the noise reduction system of the present invention. Each of the multiple parallel inputs is connected to an input amplifier in the analog averaging circuit which combines the input signals utilizing an analog averaging technique. The output of the analog averaging circuit is connected to a variable gain amplifier, the gain of which is adjusted in accordance with the output of a digital logic averaging circuit. The digital logic averaging circuit has a plurality of inputs corresponding to the number of inputs to the analog averaging circuit. These inputs to the digital logic averaging circuit are provided by the amplifiers of the analog averaging circuit. The digital logic averaging circuit then examines the signal configuration of the input signals and adjusts the gain of the variable gain amplifier in accordance with the coincidence of instantaneous positive or negative voltages on all the multiple parallel inputs of the digital logic averaging circuit. Thus, the output of the variable gain amplifier is adjusted in accordance with the true signal received by the noise reduction system over the multiple parallel inputs.

More particularly, the multiple parallel inputs of the noise reduction system are connected to an equivalent number of amplifiers in the analog averaging circuit resulting in an increase in the noise level by a factor of the square root of N whereas the actual true signal will be amplified N times, i.e., by a very large factor such as ten thousand times. These amplified signals can also be sent through logrithmic amplifiers which selectively amplify the low level signals without further amplification of the high level signals. At this stage, the outputs from these amplifiers are connected to the digital logic averaging circuit which again includes an equivalent number of amplifiers. The output from each of these amplifiers is coupled to 2 N comparators which will examine the polarity of each of the parallel input signals. If identical polarity is present at each instant from all the inputs to the digital logic averaging circuit, the signal will be regarded as a true signal whereas, in instances in which the signal does not have identical polarity the signal is rejected as noise. Two AND gates are connected to the outputs of the comparators, one of which detects positive signals and the other of which detects negative signals. The outputs of these AND gates are then connected to an OR circuit, the output of which is provided to the variable gain amplifier. The output of the OR circuit adjusts the gain of the variable gain amplifier so that the variable gain amplifier magnifies the portion of the signal from the analog averaging circuit in which the true signal component is expected.

BRIEF DESCRIPTIONS OF THE DRAWINGS

DETAILED DESCRIPTION OF THE INVENTION

Figure 1:
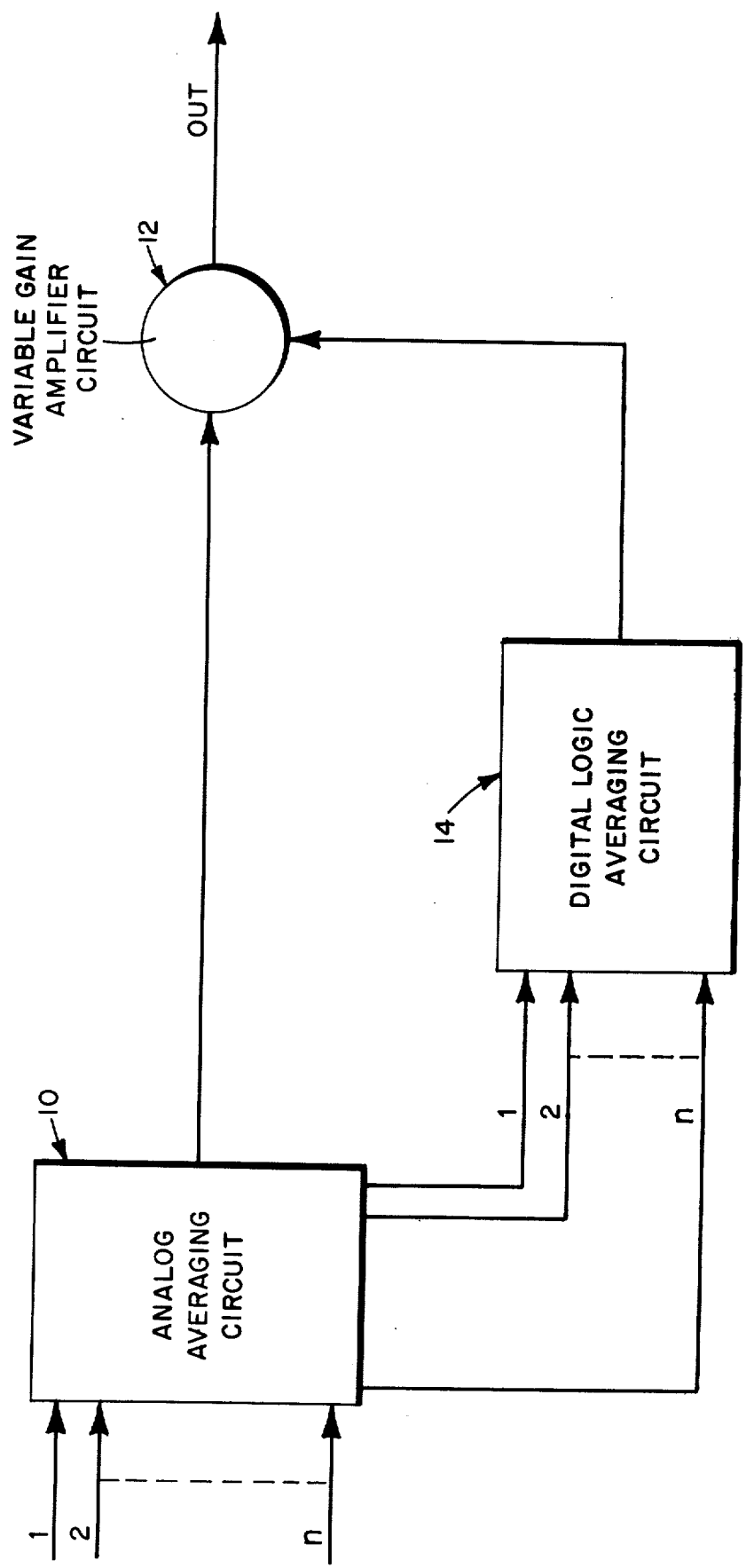
FIG. 1 is a basic block diagram of the noise reduction system of the present invention.

The multiple parallel input noise reduction system of the present invention is shown in block diagram form in FIG. 1. A plurality of multiple parallel inputs 1, 2, . . . N-1,N are shown connected to the analog averaging circuit 10. Each of the multiple parallel inputs 1, 2, . . . N-1,N provides an input signal to the analog averaging circuit 10. For example, if the noise reduction system of the present invention is used to measure the electric signals generated by the heart of a human being, a plurality of surface electrodes could be located in a small disk and placed upon the outer skin of the human being. These multiple electrodes would provide a plurality of parallel input signals on the multiple parallel inputs 1, . . . N-1,N of the analog averaging circuit 10. Of course, the noise reduction system shown in FIG. 1 can also be used to detect various other biologic signals like those arising from the central nervous system, signals in the field of space exploration and sound engineering, signals generated in electron spin resonance circuits, etc. Thus, the noise reduction system of the present invention can be used to detect low level signals in various environments by providing a plurality of probes to supply multiple parallel input signals to the analog averaging circuit 10.

The analog averaging circuit 10 amplifies in parallel the input signals on the inputs 1, . . . N-1,N. The amplified input signals are then combined together to form an output signal which has an amplification factor N whereas the noise increases by a factor of the square root of N. The signal is then supplied to the variable gain amplifier 12.

The amplified parallel input signals from the analog averaging circuit 10 are supplied to the digital logic averaging circuit 14 as illustrated in FIG. 1. The digital logic averaging circuit 14 examines the polarity of all the input signals on the inputs 1, . . . N-1,N to determine whether the polarity of these input signals is the same. If all the input signals on input 1, . . . N-1,N at a particular instant in time are positive, the digital logic averaging circuit generates an output signal which indicates that the input signal at that instant of time is a true signal. Similarly, if all the input signals are negative at a particular instant of time, the digital logic averaging circuit generates an output signal indicating that the input signal is a true signal. The output signal of the digital logic averaging circuit is then connected to the variable gain amplifier 12 to adjust the gain of the variable gain amplifier 12 in accordance with the determination of the existence of a true signal. In other words, the digital logic averaging circuit 14 in combination with the variable gain amplifier 12 amplifies the portion of the multiple parallel input signals where the low level input signal is expected. The output from the variable gain amplifier 12 is then connected to various well known control and measuring circuits.

Figure 2:
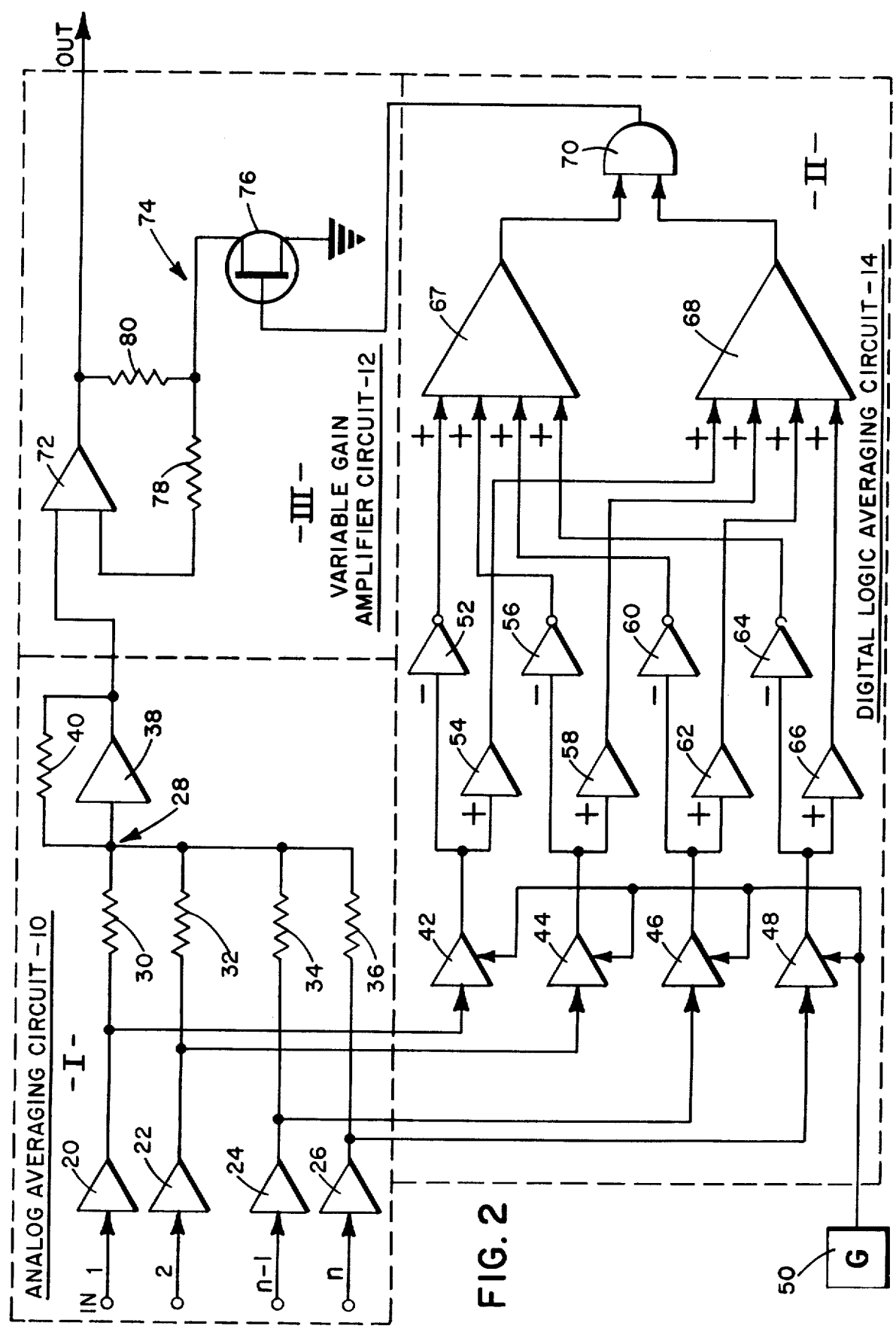
FIG. 2 is a circuit diagram of the noise reduction system of FIG. 1 illustrating the structure of each of the basic components.

Turning now to the circuit diagram illustrated in FIG. 2, the analog averaging circuit 10 includes a plurality of input amplifiers 20, 22, 24 and 26 for amplifying the input signals on the inputs 1, . . . N-1,N. The input amplifiers 20, 22, 24 and 26 may be 10 k amplifiers for amplifying the input signals by a factor of ten thousand. Well known filters (not shown) may be associated with the input amplifiers 20, 22, 24 and 26 to filter the input signals. As illustrated in FIG. 2, four different input signals are provided to the analog averaging circuit 10. The outputs of the input amplifiers 20, 22, 24 and 26 are connected to a summing node 28 through a resistive network including reistors 30, 32, 34 and 36. Although not shown in FIG. 2, the outputs of the input amplifiers 20, 22, 24 and 26 may also be connected to a plurality of logrithmic amplifiers for amplifying the low level signals without further amplification of high level signals. The combined signal at summing node 28 is amplified by amplifier 38 having feedback resistor 40. With N number of input amplifiers 20, 22, 24 and 26, the output signal from amplifier 38 results in an increase in the noise level by a factor of the square root of N while the actual true input signal will be amplified N times, e.g., ten thousand times. This output signal is then supplied to the variable gain amplifier 12 as shown in FIG. 2.

The outputs of the input amplifiers 20, 22, 24 and 26 are also connected to the inputs of a plurality of sample and hold amplifiers 42, 44, 46 and 48 of the digital logic averaging circuit 14. These sample and hold amplifiers 42, 44, 46 and 48, have a sampling frequency which is specified by pulse generator 50. This stores the result for examination of polarity for all the input signals of the noise reduction system. As shown in FIG. 2, there are four inputs to the analog averaging circuit and, therefore, there are four sample and hold amplifiers for storing the simultaneously acquired polarity of the four different input signals. Sample and hold amplifier 42 holds the polarity of the input signal on input 1 to the input amplifier 20 of the analog averaging circuit 10. Similarly, the sample and hold amplifiers 44, 46 and 48 hold the polarity of the input signals on the inputs 2, N-1 and N of the input amplifiers 22, 24 and 26 of the analog averaging circuit 10.

The outputs of the sample and hold amplifiers 42, 44, 46 and 48 are connected to a comparator circuit. The comparator circuit includes a pair of comparators connected to each of the outputs of the sample and hold amplifiers 42, 44, 46 and 48. For example, the output of sample and hold amplifier 42 is connected to a comparator and inverter 52 which compares the output of the sample and hold amplifier 42 to a reference voltage to determine if it is negative and inverts the signal. The output of the sample and hold amplifier is also connected to a second comparator 54 which compares the output of this sample and hold amplifier to determine if it is positive and does not invert the signal. Similarly, the outputs of sample and hold amplifiers 44, 46 and 48 are each respectively connected to a comparator and inverter 59, 60 and 64 as well as a second comparator 58, 62 and 66. The outputs of the comparator and inverters 52, 56, 60 and 64 are connected to an AND gate 67 whereas the outputs of the comparators 54, 58, 62 and 66 are connected to another AND gate 68. The comparator circuit consisting of 2 N comparators examines each of the input signals via the sample and hold amplifiers to determine if identical polarity is present at each instant of time from all the inputs. If all the input signals have a negative polarity, the comparator/inverters 52, 56, 60 and 64 fulfill the coincidence condition of the AND gate 67 which then supplies an output signal to the OR gate 70. Similarly, if all the input signals are positive, the comparators 54, 58, 62 and 66 fulfill the coincidence condition of the AND gate 68 which supplies a signal to the OR gate 70. Thus, identical polarity from all the inputs 1, . . . N-1,N of the analog averaging circuit 10 is regarded as a true signal by the digital logic averaging circuit 14 while signals with non-identical polarity are rejected as noise by the comparator circuit and the logic circuit consisting of the AND gate 67 and 68 and the OR gate 70.

The output from the amplifier 38 of the analog averaging circuit 10 is connected to a variable gain amplifier 72 of the variable gain amplifier circuit 12. The variable gain amplifier 72 has a gain control circuit 74 including FET transistor 76 and biasing resistors 78 and 80. The FET transistor 76 of the gain control circuit 74 has its gate electrode connected to the output of the OR gate 70 of the digital logic averaging circuit 14. When a true signal is detected by the digital logic averaging circuit 14, the OR gate 70 supplies a signal to the FET transistor 76 which enables the gain control circuit 74 to adjust the gain of the variable gain amplifier 72. The occurrence of a true signal enables the gain control circuit 74 to increase the amplification of the variable gain amplifier 72 so that the portion of the signal from the amplifier 38 of the analog averaging circuit 10 in which the low level input signal is expected is magnified by the variable gain amplifier 72. In this manner, the variable gain amplifier circuit 12 provides a moment-to-moment amplification of the true low level input signal received by the analog averaging circuit 10 and rejects the noise component by adjusting the gain of the variable gain amplifier circuit 12 in accordance with the detection of the true signal by the digital logic averaging circuit 14. The output of the variable gain amplifier 72 provides an output signal which corresponds to the true low level input signal received by the noise reduction system of the present invention.

The operation of the noise reduction system of the present invention is apparent from the above description. Multiple parallel input signals are amplified in parallel by the input amplifiers 20, 22, 24 and 26 and combined together in the analog averaging circuit 10 to provide a signal having increased gain by a factor N while noise increases by a factor of the square root of N. The parallel outputs of the input amplifiers 20, 22, 24 and 26 are connected to a comparator circuit which examines the polarity of the respective input signals and generates a true signal when the polarity of all the input signals is identical. The true signal is then used by the gain control circuit 74 of the variable gain amplifier circuit 12 to adjust the gain of the variable gain amplifier 72. The variable gain amplifier amplifies the output signal from the output amplifier 38 of the analog averaging circuit 10. In this manner, the multiple parallel input noise reduction system of the present invention rejects noise and detects low level input signals.

Although illustrative embodiments of the invention have been described in detail with reference to the accompanying drawings, it is to be understood that the invention is not limited to those precise embodiments and that various changes and modifications may be effected therein by one skilled in the art without departing from the scope or spirit of the invention.

I claim:

1. A multiple parallel input noise reduction system for amplifying a low level electrical signal comprising:
   a multiple number of parallel inputs each transmitting an input signal corresponding to the low level electrical signal;
   analog averaging means connected to said multiple number of parallel inputs for amplifying each of the input signals and combining the input signals together to form a first output signal;
   digital logic averaging means connected to said analog averaging means for examining the instantaneous polarity of each of the amplified input signals from said analog averaging means and generating a coincidence signal in the event all the amplified input signals have the same instantaneous polarity; and
   variable gain amplifier means connected to said analog averaging means for amplifying the first output signal to generate a second output signal, said variable gain amplifier means having gain control means responsive to the coincidence signal from said digital logic averaging means for adjusting the gain of said variable gain amplifier means to amplify those portions of the first output signal corresponding to the true low level electrical signal.

2. The noise reduction system according to claim 1 wherein said analog averaging means comprises an input amplifier connected to each of said parallel inputs, the outputs from said input amplifiers being connected to an output amplifier which amplifies the combined outputs of said input amplifiers and provides the first output signal.

3. The noise reduction system according to claim 2 wherein said digital logic averaging means comprises a number of sample and hold amplifiers corresponding to the number of said parallel inputs, one of said sample and hold amplifiers being connected to the output of each of said input amplifiers, each of said sample and hold amplifiers being connected to a first comparator for examining the amplified input signals for positive polarity and a second comparator for examining the amplified input signals for negative polarity.

4. The noise reduction system according to claim 3 wherein said digital logic averaging means further comprises first AND gate means connected to the outputs of said first comparators for generating the coincidence signal in response to the coincidence of positive polarity from all said first comparators, second AND gate means connected to the outputs of said second comparators for generating the coincidence signal in response to the coincidence of negative polarity from all said second comparators and OR gate means connected to said first and second AND gate means for supplying the coincidence signal to said gain control means of said variable gain amplifier means.

5. The noise reduction system according to claim 1 wherein said digital logic averaging means comprises first comparator means for examining the amplified input signals for positive polarity and second comparator means for examining the amplified input signals for negative polarity.

6. The noise reduction system according to claim 5 wherein said digital logic averaging means further comprises logic means connected to said first and second comparator means for providing a coincidence signal to said gain control means in the event said first and second comparators determine that the polarity of all the input signals is positive or negative, respectively.

* * * * *